United States Patent [19]

Takaki et al.

[11] Patent Number: 4,656,306

[45] Date of Patent: Apr. 7, 1987

[54] PREPARATION PROCESS OF CINNAMATE ESTER

[75] Inventors: Usaji Takaki, Fujisawa; Isamu Sudo; Toshio Matsuhisa, both of Yokohama, all of Japan

[73] Assignee: Mitsui Toatsu Chemicals, Incorporated, Tokyo, Japan

[21] Appl. No.: 803,162

[22] Filed: Dec. 2, 1985

[30] Foreign Application Priority Data

Dec. 10, 1984 [JP] Japan .................................. 59-259253

[51] Int. Cl.$^4$ ........................ C07C 69/76; C07C 51/14
[52] U.S. Cl. .................................... 560/104; 562/406
[58] Field of Search ......................... 560/104; 562/406

[56] References Cited

U.S. PATENT DOCUMENTS 3,530,168  9/1970  Biale ..................................... 560/104

FOREIGN PATENT DOCUMENTS 7021342  4/1982  Japan .................................... 560/104

Primary Examiner—Paul J. Killos
Attorney, Agent, or Firm—Fisher, Christen & Sabol

[57] ABSTRACT

Disclosed herein is a process for preparing a corresponding cinnamate ester by the reaction of a styrene compound, carbon monoxide, an alcohol and oxygen by using a main catalyst composed of (a) a platinum group metal or a compound thereof and (b) a copper or iron compound and in the presence of a promoter, wherein the concentration of the metal of the component (a) is controlled at $5.5 \times 10^{-4}$ gram atom/liter or below in the liquid reaction mixture and further the ratio of the component (b) to the metal of the component (a) is maintained at 50 moles/gram atom or above so as to carry out the reaction.

5 Claims, No Drawings

PREPARATION PROCESS OF CINNAMATE ESTER

BACKGROUND OF THE INVENTION

(1) Field of the Invention

This invention relates to a process for preparing cinnamate esters by the reaction of styrene compounds, carbon monoxide, alcohols and oxygen.

(2) Description of the Prior Art

Cinnamate esters have found wide-spread commercial utility as perfumes and raw materials therefor owing to their inherent aroma. They are also important as raw materials for agricultural chemicals and photosensitive resins.

Cinnamic acid has conventionally been produced on small scales by using benzaldehyde and derivatives of acetic acid as principal raw materials. This process is however not preferred from the industrial viewpoint since it requires such costly raw materials. As processes permitting use of more economical raw materials, several processes have been proposed to prepare a cinnamate ester by reacting a styrene compound, carbon monoxide, an alcohol and oxygen in the presence of a catalyst (see, for example, Japanese Patent Laid-Open No. 15242/1981, etc.).

In these processes, however, the activities of catalysts are still low and therefore expensive metals have to be used in large amounts as the catalysts. For these reasons, they have not yet been practiced on any industrial scales.

SUMMARY OF THE INVENTION

The object of the present invention is to provide an industrially advantageous process for preparing a cinnamate ester from a styrene compound, carbon monoxide, an alcohol and oxygen as raw materials. More specifically, it is to establish a process for preparing a cinnamate ester with a high turnover frequency (i.e., the number of moles of cinnamate ester formed per gram atom of the metal of the first component of the catalyst and per hour of the reaction time, and therefore expressed in terms of mole/(gram atom·hour)) by increasing the activity of the catalyst, decreasing the amount of an expensive metal to be used as a component of the catalyst and thus achieving a satisfactorily high reaction performance.

The present inventors have made intensive effort to accomplish the aforesaid object and obtained the following findings. Namely, a corresponding cynamate ester is prepared by the reaction of a styrene compound, carbon monoxide, an alcohol and oxygen in the presence of a main catalyst comprising a platinum group metal or a compound thereof as the first component and a copper or iron compound as the second component. When this reaction is carried out in such a way that the concentration of the metal of the first component is controlled below a specified concentration in the liquid reaction mixture and besides the ratio of the second component to the metal of the first component is maintained above a specified ratio, a high reaction performance can be obtained and thus the cynamate ester can be prepared with a high turnover frequency. The present invention has been completed on the basis of this discovery.

Specifically, the present invention provides a process for preparing a corresponding cinnamate ester by the reaction of a styrene compound, carbon monoxide, an alcohol and oxygen by using a main catalyst composed of (a) a platinum group metal or a compound thereof and (b) a copper or iron compound and in the presence of a promoter, wherein the concentration of the metal of the component(a) is controlled at $5.5 \times 10^{-4}$ gram atom/liter or below in the liquid reaction mixture and further the ratio of the component(b) to the metal of the component(a) is maintained at 50 moles/gram atom or above so as to carry out the reaction.

DETAILED DESCRIPTION OF THE PREFERRED EMBODIMENTS

As specific styrene compounds useful in the practice of the process of the present invention, may be mentioned styrene; alkyl derivatives of styrene, such as α-methylstyrene, β-methylstyrene, α-ethylstyrene, β-ethylstyrene, o-methylstyrene, m-methylstyrene, p-methylstyrene, m-ethylstyrene, p-ethylstyrene, p-tert-butylstyrene and β-methyl-p-isopropylstyrene; and other styrene derivatives having, on their aromatic rings, substituent groups which do not impair the intended reactions, such as p-chlorostyrene, p-methoxystyrene and 3,4-dimethoxystyrene.

As exemplary alcohols, may be mentioned methanol, ethanol, propanol, butanol, pentanol, octanol, cyclopentanol, cyclohexanol, phenol, benzylalcohol, ethylene glycol, polyethylene glycol, propylene glycol, etc. These alcohols may contain substitutents which do not impair the respective reactions, such as halogen, alkoxy groups and the like. These alcohols may each be used in an amount of 0.5–100 parts or preferably 1–50 parts by mole per mole of the styrene compound. They may be used not only as reaction raw materials but also as solvents.

The partial pressure of carbon monoxide is 51 atomspheres (absolute pressure, the same shall apply hereunder) or less, or preferably in the range of 0.005–40 atmospheres.

The partial pressure of oxygen is 51 atmospheres or less, or preferably in the range of 0.002–30 atmospheres. Either pure oxygen or air may be used as the source of oxygen.

The gaseous mixture of carbon monoxide and oxygen may be used by diluting it with an inert gas such as nitrogen and argon in order to keep the gaseous mixture out of the range of explosion.

In the practice of the process of the present invention, the presence of carbon dioxide in the reaction system will cause the performance of the reaction and the activity of the catalyst to further enhance. There have been no precedents in which the reaction was successfully effected by the addition of carbon dioxide to the reaction system in the preparation of a cinnamate ester by reacting a styrene compound, carbon monoxide, an alcohol and oxygen.

The partial pressure of carbon dioxide is 300 atmospheres or below, or preferably in the range of 0.1–100 atmospheres. It is however preferred to control the partial pressure of carbon dioxide at 10% (by pressure ratio) or above relative to the total pressure of the reaction, in other words, to maintain the concentration of carbon dioxide in the gaseous reaction mixture at 10% by volume or above, or more preferably in the range of 10%–98%. If the concentration of carbon dioxide is lower than 10%, the effect of carbon dioxide cannot be brought about. Any concentrations of carbon dioxide higher than 98% lead to lowered concentrations of carbon monoxide and oxygen, thereby retarding the reaction velocity. Most preferably, the concentration of carbon dioxide may be within the range of 15–95%.

Carbon monoxide and oxygen, and, if used, carbon dioxide and an inert gas may be charged together in their respective required amounts to the reactor. Alternatively, desired gases may be additionally fed either continuously or intermittently or their mixed gas may be caused to flow either continuously or intermittently.

In the reaction according to the process of the present invention, the alcohol as a raw material may practically be used as a solvent. Other solvents may however be used so long as they do not impair the reaction. Illustrative of such other solvents are ethers such as diethyl ether, dipropyl ether, methyl ethyl ether, phenyl ethyl ether, diphenyl ether, tetrahydrofuran, dioxane, ethylene glycol diethyl ether and tetraethylene glycol dimethyl ether, ketones such as acetone, methyl ethyl ketone and acetophenone, esters such as methyl acetate, ethyl acetate and methyl propionate, aromatic hydrocarbons such as benzene, toluene, p-xylene, ethylbenzene, chlorobenzene and dichlorobenzene and their substituted compounds, aliphatic and alicyclic hydrocarbons such as n-hexane, n-pentane and cyclohexane, carbonates such as propylene carbonate and dimethyl carbonate, nitriles such as acetonitrile and benzonitrile, aromatic nitro compounds such as nitrobenzene, amide compounds such as dimethylformamide, sulfone compounds such as sulfolane, etc.

In the process of the present invention, a dehydrating agent may exist in the reaction system so as to remove the water formed. As the dehydrating agent may be mentioned Molecular Sieve, silica gel, methyl orthoformate, acetic anhydride or the like.

The main catalyst used in the process of the present invention is composed of (a) a platinum group metal or a compound thereof as the first component and (b) a copper or iron compound as the second component.

As the platinum group metal or its compound as the first compound of the catalyst, may be mentioned a metal such as ruthenium, rhodium, palladium, osmium, iridium or platinum, or its halide, nitrate, sulfate, phosphate, its salt of organic carboxylic acid such as acetic acid, or its oxide. Of these, palladium or palladium chloride is particularly preferred. Complex compounds, e.g., dibenzylidene aceton complexes, benzonitrile complexes, acetylacetonate complexes, amine complexes, etc. of these metals or their compounds may be used.

These metals or their compounds may be supported on a carrier for use. As examples of such a carrier may be mentioned activated carbon, graphite, alumina, silica, silica-alumina, magnesia, zeolite, Molecular Sieve, or an ion-exchange resin.

These platinum group metals or their compounds may each be used in its metallic concentration in the liquid reaction mixture comprising a styrene compound, an alcohol, a solvent and the like at $5.5 \times 10^{-4}$ gram atom/liter or below, or preferably in the range of $5.5 \times 10^{-4}$–$5.5 \times 10^{-7}$ gram atom/liter.

The copper or iron compound as the second component of the catalyst may include chlorides, nitrates, sulfates or phosphates of copper or iron, copper or iron salts of organic carboxylic acids such acetic acid, or the like. Particularly preferred is the chloride. Two or more of these compounds may be used simultaneously in combination. These compounds may each be used in such an amount that the ratio of the compound to the metal of the first component of the catalyst may be maintained at 50 moles/gram atom or above. Any lower ratios than this value will cause a substantial reduction in the activity of the catalyst and in some cases may even suppress the reaction. Even if the concentration of the metal of the first component is increased, the activity of the catalyst will not increase and the performance of the reaction will also be degraded. The preferred ratio may be in the range of 50–5,000 moles/gram atom.

The promoters used in the process of the present invention may embrace (1) hydroxides, carbonates or organic acid salts of alkali metals or alkaline earth merals, (2) organic acid salts of aluminum, (3) tertiary amines, or (4) compounds of at least one metal selected from Groups 4A, 7A, 8A (the iron group only), 1B and 2B of the periodic table published by International Union of Pure and Applied Chemistry (hereinafter simply referred to as the periodic table).

As regards the promoters, specific examples of the hydroxides, carbonates or organic acid salts of alkali metals or alkaline earth metals categorized in the above (1) may include hydroxides such as sodium hydroxide, potassium hydroxide, calcium hydroxide and barium hydroxide, carbonates such as sodium carbonate, sodium hydrogencaronate, potassium carbonate, lithium carbonate and magnesium carbonate, and aliphatic or aromatic mono- or poly-valent carboxylic acid salts such as sodium acetate, potassium acetate, calcium acetate, sodium propionate, potassium stearate, calcium succinate, sodium phenylacetate, potassium benzoate and sodium phthalate.

As the organic acid salts of aluminum categorized in the above (2) may be mentioned aluminum acetate, basic aluminum acetate, aluminum propionate, aluminum stearate, aluminum benzoate and the like.

As the tertiary amines categorized in the above (3) may be mentioned trimethylamine, triethylamine, tributylamine, triisopropylamine, diethylmethylamine, dimethylpropylamine, allyldiethylamine, dimethylbenzylamine, dicyclohexylethylamine, dimethylcyclohexylamine and the like.

Illustrative of the compounds of at least one metal selected from Groups 4A, 7A, 8A (the iron group only), 1B and 2B categorized in the above (4) may specifically be the following compounds of such metals as titanium, zirconium, manganese, technetium, rhenium, iron, cobalt, nickel, copper, silver, gold, zinc, cadmium and mercury: the oxides, hydroxides, halides and carbonates; the salts of mono- or poly-valent aliphatic carboxylic acids such as acetic acid, propionic acid, stearic acid, succinic acid and phenylacetic acid; the salts of aromatic carboxylic acids such as benzoic acid and phthalic acid; or the complex compounds such as acetylacetonate complexes and cyclopentadienyl complexes.

Two or more of these promoters may be used at the same time. In some cases, it is possible to use compounds capable of forming the above-described compounds in the reaction system in combination.

The promoters may each be used in an amount in the range of 0.00001–20 moles per mole of the styrene compound used as a raw material, with the range of 0.0001–2.0 moles per mole of the styrene compound being preferred.

In the process of the present invention, the total pressure of the reaction may generally be in the range of 1–500 atmospheres or preferably in the range of 1–300 atmospheres. The reaction temperature may range from room temperature to 200° C. or preferably from 40° to 160° C. The reaction time varies depending on the reaction conditions, but may generally range from 0.01 to 24 hours with the range of 0.05–10 hours being preferred.

After completion of the reaction, the intended cinnamate ester can be isolated from the liquid reaction mixture by a routine technique for isolation such as distillation or extraction.

According to the process of the present invention, a cinnamate ester can be prepared by using an expensive metal of the first component of the catalyst in extraordinarily low concentrations or in extremely small amounts compared with the prior art. A very high mole number of a cinnamate ester is formed per gram atom of the metal of the first component. Further, the rate of reaction is sufficiently high and also the turnover frequency (mole/(gram atom·hour)) of the metal of the first component is remarkably high. Such a high turnover frequency brought about by the practice of the present invention is very beneficial from an industrial point of view in the preparation of a cinnamate ester from a styrene compound, carbon monoxide, an alcohol and nitrogen as raw materials.

The process of the present invention will hereinafter be described more specifically by the following Examples and Comparative Examples.

EXAMPLE 1

In a 200-ml autoclave, in which its inside walls and accessories were protected with glass at areas where they were brought into contact with liquid reaction mixtures, were charged 10.4 g (100 millimoles) of styrene, 3.6 mg (0.020 millimole) of palladium chloride, 672 mg (5.00 millimoles) of cupric chloride, 2.74 g (12.5 millimoles) of zinc acetate dihydrate. Then, methanol was added thereto to make the total volume to 50 ml. The concentration of palladium was $4.0 \times 10^{-4}$ gram atom/liter and the ratio of cupric chloride to palladium was 250 moles/gram atom. The reaction was effected at 100° C. for 3 hours, while maintaining the total pressure at 51 atmospheres and causing a mixed gas consisting of carbon monoxide, oxygen and nitrogen in a volume ratio of 10.7:5.4:83.9 to pass continually through the autoclave at a flow rate of 400 ml/minutes (under standard conditions) at the outlet of the autoclave. The outlet gas was discharged through a reflux condenser. After completion of the reaction, the autoclave was cooled and its pressure was released. Then, the liquid reaction mixture was taken out of the autoclave and filtered. The composition of the filtrate was analyzed by high-speed liquid chromatography.

The filtrate contained 19.9 millimoles of styrene, 71.4 millimoles of methyl cinnamate and 4.1 millimoles of dimethyl phenylsuccinate. The conversion of styrene was 80.1%, the yield of methyl cinnamate was 89.2% based on the consumed styrene, and the yield of by-produced dimethyl phenylsuccinate was 5.1%. The mole number of the methyl cinnamate formed per gram atom of palladium was 3,570 and the turnover frequency of palladium was 1,190 moles/(gram atom·hour).

EXAMPLE 2

Raw materials were charged to the same reactor and in exactly the same manner as described in Example 1 except that the gaseous components were not caused to flow through the reactor, but carbon monoxide was introduced thereinto up to a pressure of 24 atmosphere and thereafter a mixed gas consisting of oxygen and nitrogen, in which the content of oxygen was 6% by volume, was fed with an additional increased pressure of 192 atmospheres so as to achieve an oxygen partial pressure of 11.5 atmospheres. The contents were increased in temperature with stirring to 100°–130° C. at which the reaction was effected for 17 minutes. The conversion of styrene was 54.6% and the yield of methyl cinnamate was 66.5% based on the consumed styrene. The yield of dimethyl phenylsuccinate was 6.3%.

1,820 moles of methyl cinnamate was formed per gram atom of palladium and the turnover frequency of palladium was 6,410 moles/(gram atom·hour).

Comparative Example 1

The reaction was effected in exactly the same manner as described in Example 2 except that the amount of cupric chloride was changed to 27.0 mg (0.20 millimole). The concentration of palladium was $4.0 \times 10^{-4}$ gram atom/liter and the ratio of cupric chloride to palladium was 10.0 moles/gram atom. The conversion of styrene was 1.5% and the formation of methyl cinnamate was not observed. Thus, the turnover frequency of palladium was zero.

Comparative Example 2

The reaction was effected in exactly the same manner as described in Example 2 except that the amounts of palladium chloride and cupric chloride were changed respectively to 24.3 mg (0.137 millimole) and 188.5 mg (1.40 millimoles). The concentration of palladium was $2.74 \times 10^{-3}$ gram atom/liter and the ratio of cupric chloride to palladium was 10.2 moles/gram atom.

The conversion of styrene was 52.9% and the yield of methyl cinnamate was 19.3% based on the consumed styrene. The yield of dimethyl phenylsuccinate was 20.1% and many other by-products were also formed. Only 74.5 moles of cinnamate ester was formed per gram atom of the palladium used. The turnover frequency of palladium was as low as 263 moles/(gram atom·hour).

EXAMPLES 3–10

The reactions were effected in exactly the same manner as described in Example 2 except that the lieu of the zinc acetate dihydrate employed in Example 2, the promoters given in Table 1 were used in their respective amounts. The concentrations of palladium and the ratios of cupric chloride to palladium were not changed and were respectively $4.0 \times 10^{-4}$ gram atom/liter and 250 moles/gram·atom. The results are given in Table 1.

TABLE 1

| Example | Promoter Type | Amount (millimole) | Methyl cinnamate formed (millimole) | Methyl cinnamate formed per gram atom of palladium (mole/gram atom) | Palladium turnover frequency (mole/gram atom · hr) |
|---|---|---|---|---|---|
| Example 3 | Potassium acetate | 12.5 | 21.1 | 1,060 | 3,720 |

TABLE 1-continued

| Example | Promoter Type | Amount (millimole) | Methyl cinnamate formed (millimole) | Methyl cinnamate formed per gram atom of palladium (mole/gram atom) | Palladium turnover frequency (mole/gram atom · hr) |
|---|---|---|---|---|---|
| Example 4 | (CH$_3$COOK) Calcium hydroxide (Ca(OH)$_2$) | 5.0 | 15.8 | 790 | 2,790 |
| Example 5 | Basic aluminum acetate tetra-hydrate (Al$_2$O(CH$_3$COO)$_4$—4H$_2$O) | 6.2 | 16.4 | 820 | 2,890 |
| Example 6 | Triethylamine ((C$_2$H$_5$)$_3$N) | 5.1 | 11.5 | 575 | 2,030 |
| Example 7 | Titanium (IV) oxyacetyl-acetonate (TiO(acac)$_2$) | 5.0 | 36.3 | 1,815 | 6,410 |
| Example 8 | Manganese acetate tetra-hydrate (Mn(CH$_3$COO)$_2$—4H$_2$O) | 12.5 | 45.0 | 2,250 | 7,940 |
| Example 9 | Nickel benzoate trihydrate (Ni(C$_6$H$_5$COO)$_2$—3H$_2$O) | 12.5 | 40.3 | 2,020 | 7,110 |
| Example 10 | Zinc hydroxide (Zn(OH)$_2$) | 5.0 | 25.9 | 1,300 | 4,570 |

Note:
"acac" signifies acetylacetonate.

EXAMPLE 11

The reaction was carried out in exactly the same manner as described in Example 2 except that 1.62 g (10.0 millimoles) of ferric chloride and ethanol were used in place respectively of the cupric chloride and methanol used in Example 2 and the reaction time was changed to 20 minutes. The concentration of palladium was $4.0 \times 10^{-4}$ gram atom/liter and the ratio of ferric chloride to palladium was 500 moles/gram atom. 15.7 millimoles of ethyl cinnamate was formed. Thus, the mole number of the ethyl cinnamate formed per gram atom of palladium was 785, while the turnover frequency of palladium was 2,360 moles/(gram atom· hour).

EXAMPLE 12

The reaction was carried out in exactly the same manner as described in Example 2 except that the amounts of styrene and palladium chloride were changed respectively to 5.21 g (50.0 millimoles) and 2.0 mg (0.011 millimole). The concentration of palladium was $2.2 \times 10^{-4}$ gram atom/liter and the ratio of cupric chloride to palladium was 455 moles/gram atom.

The conversion of styrene was 70.3% while the yield of methyl cinnamate was 62.5% based on the consumed styrene.

Methyl cinnamate was formed in an amount of 2,000 moles per gram atom of palladium. The turnover frequency of palladium was 7,050 moles/(gram atom· hour).

EXAMPLE 13

The reaction was carried out in exactly the same manner as described in Example 2 except that the amount of cupric chloride was changed to 2.69 g (20.0 millimoles). The concentration of palladium was $4.0 \times 10^{-4}$ gram atom/liter and the ratio of cupric chloride to palladium was 1,000 miles/gram·atom.

The conversion of styrene was 82.4% while the yield of methyl cinnamate was 43.5% based on the consumed styrene. Methyl cinnamate was formed in an amount of 1,790 moles per gram atom of palladium. Thus, the turnover frequency of palladium was 6,320 moles/(gram atom·hour).

EXAMPLE 14

The reaction was carried out by the gas flow method in exactly the same manner as described in Example 1 except that the amount of cupric chloride was changed to 1.35 g (10.0 millimoles).

The concentration of palladium was $4.0 \times 10^{-4}$ gram atom/liter and the ratio of cupric chloride to palladium was 500 moles/gram·atom.

The conversion of styrene was 92.4% while the yield of methyl cinnamate was 76.0% based on the consumed styrene. Methyl cinnamate was formed in an amount of 3,510 moles per gram atom of palladium. The turnover frequency of palladium was 1,170 moles/(gram atom· hour).

EXAMPLE 15

The reaction was carried out by the gas flow method in exactly the same manner as described in Example 1 except that 5% Pd/C (catalyst composed of 5% by weight of palladium carried on activated carbon) was used in an amount of 42.6 mg (equivalent to 0.02 milli-gram atom of palladium) in place of the palladium chloride used in Example 1.

The concentration of palladium was $4.0 \times 10^{-4}$ gram atom/liter and the ratio of cupric chloride to palladium was 250 moles/gram·atom.

The conversion of styrene was 57.6% while the yield of methyl cinnamate was 86.5% based on the consumed styrene. The yield of dimethyl phenylsuccinate was 6.7%.

The mole number of methyl cinnamate formed per gram atom of palladium was 2,490 and the turnover frequency of palladium was 830 moles/(gram atom·hour).

EXAMPLE 16

The reaction was carried out in exactly the same manner as described in Example 2 except that p-chlorostyrene was used in place of styrene. Then, 19.3 millimoles of methyl p-chlorocinnamate was formed. Thus, the methyl p-chlorocinnamate was formed in an amount of 965 moles per gram mole of palladium. The turnover frequency of palladium was 3,410 moles/(gram atom·hour).

EXAMPLE 17

The reaction was carried out in exactly the same manner as described in Example 1 except that the gaseous feed material was changed to a mixed gas consisting of carbon monoxide, oxygen and carbon dioxide in a volume ratio of 10.0:5.8:84.2. The conversion of styrene was 86.9% while the yield of methyl cinnamate was 90.7% based on the consumed styrene. The mole number of the methyl cinnamate formed was 3,940 per each gram atom of palladium and the turnover frequency of palladium was 1,310 moles/gram atom·hour). All of the above values were higher than those obtained in Example 1.

What is claimed is:

1. Process for preparing a corresponding cinnamate ester by the reaction of a styrene compound, carbon monoxide, an alcohol and oxygen by using a main catalyst composed of (a) a platinum group metal or a compound thereof and (b) a copper or iron compound and in the presence of a promoter, wherein the concentration of the metal of components (a) is controlled at $5.5 \times 10^{-4}$ gram atom/liter or less in the liquid reaction mixture and further the ratio of components (b) to the metal of components (a) is maintained at 50 moles/gram atom or greater so as to carry out the reaction, said promoter being a compound of at least one metal selected from Groups 4A, 7A, 8A (the iron group only), 1B and 2B of the periodic table published by International Union of Pure and Applied Chemistry, or an organic acid salt of aluminum, or a hydroxide, carbonate or organic acid salt of an alkali metal or alkaline earth metal, or a tertiary amine.

2. The process as claimed in claim 1 wherein the promoter is a compound of manganese, zinc, nickel or titanium.

3. The process as claimed in claim 1 wherein the platinum group metal or the compound thereof is a metallic palladium of a compound thereof.

4. The process as claimed in claim 1 wherein the compound of the component (b) is a copper compound.

5. The process as claimed in claim 1 wherein the above-described reaction is effected in the presence of carbon dioxide.

* * * * *